United States Patent [19]
Buchi et al.

[11] 3,932,546
[45] Jan. 13, 1976

[54] PREPARATION OF POLYENES

[75] Inventors: George H. Buchi; Roger M. Freidinger, both of Cambridge, Mass.

[73] Assignee: Massachusetts Institute of Technology, Cambridge, Mass.

[22] Filed: Feb. 8, 1974

[21] Appl. No.: 440,853

[52] U.S. Cl. .......................... 260/666 C; 260/677 R
[51] Int. Cl. ............................................. C07c 13/00
[58] Field of Search .................... 260/666 C, 677 R

[56] References Cited
UNITED STATES PATENTS

| | | | |
|---|---|---|---|
| 3,803,252 | 4/1974 | Chabardes et al. | 260/666 C |
| 3,850,991 | 11/1974 | Chabardes et al. | 260/666 C |

OTHER PUBLICATIONS

Leonhard Bikofer et al., Chem. Ber. 99, pp. 2070–2071, 1960.
Leo A. Paquette et al., J. Amer. Chem. Soc., 90:24, pp. 6783–6789, Nov. 20, 1968.
S. Braverman, Int. J. Sulfur Chemistry, Pt. C. Vol. 6, pp. 149–154, 1971.

*Primary Examiner*—Delbert E. Gantz
*Assistant Examiner*—C. E. Spresser
*Attorney, Agent, or Firm*—Arthur A. Smith, Jr.; Martin M. Santa; David G. Conlin

[57] ABSTRACT

Polyenes are synthesized from unsaturated materials having allylic hydroxyl groups, which react with imidosulfides to produce sulfones. Removal of the sulfone group, e.g. by reaction with alkyllithium and iodine, results in compounds in which the allylic carbons are joined by a double bond. The reactions take place easily over wide temperature ranges. The method is particularly advantageous in the synthesis of carotenoids from polyene alcohols, being much simpler and easier to use than previous carotenoid syntheses.

17 Claims, No Drawings

PREPARATION OF POLYENES

BACKGROUND

The invention herein described was made in the course of work performed under a grant with the National Institutes of Health.

The usefulness of polyenes, e.g. in making polymers of many uses, has long been known. Conjugated polyenes, such as isoprene, are particularly useful in making synthetic elastomers, and other materials. In spite of a great deal of interest in such compounds, the methods for synthesizing them have suffered from a number of difficulties. One early method involved the reduction of unsaturated carbonyl compounds to pinacols, replacement of the hydroxyl groups by halogens, and elimination of the halogens by zinc. This complex procedure necessitated the use of large quantities of materials, involved difficult chemical procedures, and usually resulted in poor over-all yields of the polyene. An improved method was disclosed by Kharasch et al, J. Amer. Chem. Soc., 61: 2318 (1939), which involved the alkaline condensation of organic halides, e.g. allyl chloride, to form unsaturated dimers. That method was based on the finding that halides of weakly electronegative radicals condense when treated with sodamide in liquid ammonia if there is a hydrogen atom on the carbon atom to which the halogen is attached. The Kharasch method of synthesis still suffered from a number of drawbacks. The reaction was difficult to control, in that the materials polymerized to varying degrees, giving a mixture of unsaturated cyclic and acyclic compounds of varying structure and chain length. Also, condensation would occur between the organic chloride starting materials and various carbon atoms in the desired polyene products, giving a mixture of many varieties of polyenes with many varieties of halogen compounds.

Similar problems plagued the synthesis of more complex polyenes such as the carotenoids. Carotenoids are a class of easily oxidizable, highly colored compounds that are widely distributed in plants and animals and are noted for their preferential solubility in fats and in solvents for fats. They are highly unsaturated compounds, containing a chromophoric system of conjugated double bonds in a multibranched chain of carbon atoms. Over 100 carotenoid pigments have been described, having colors which vary in accordance with the number and conjugation of the double bonds they contain. The carotenoids, especially β-carotene, are generally useful as edible dyestuffs in food and beverages, and as vitamin-A supplements in food and fodder.

While carotenoids have previously been synthesized, their preparation has required extensive and complex reaction schemes, which often result in rather low yields. While there is close structural similarity between the higher carotenoids, such as β-carotene, and shorter chain polyene alcohols, such as vitamin A, the synthesis of the carotenoids has generally followed a different and often more complicated route than the synthesis of the lower polyene alcohols. For example β-carotene is generally commercially prepared by the following scheme, shown in Isler, Carotenoids, at 480–82 (1971):

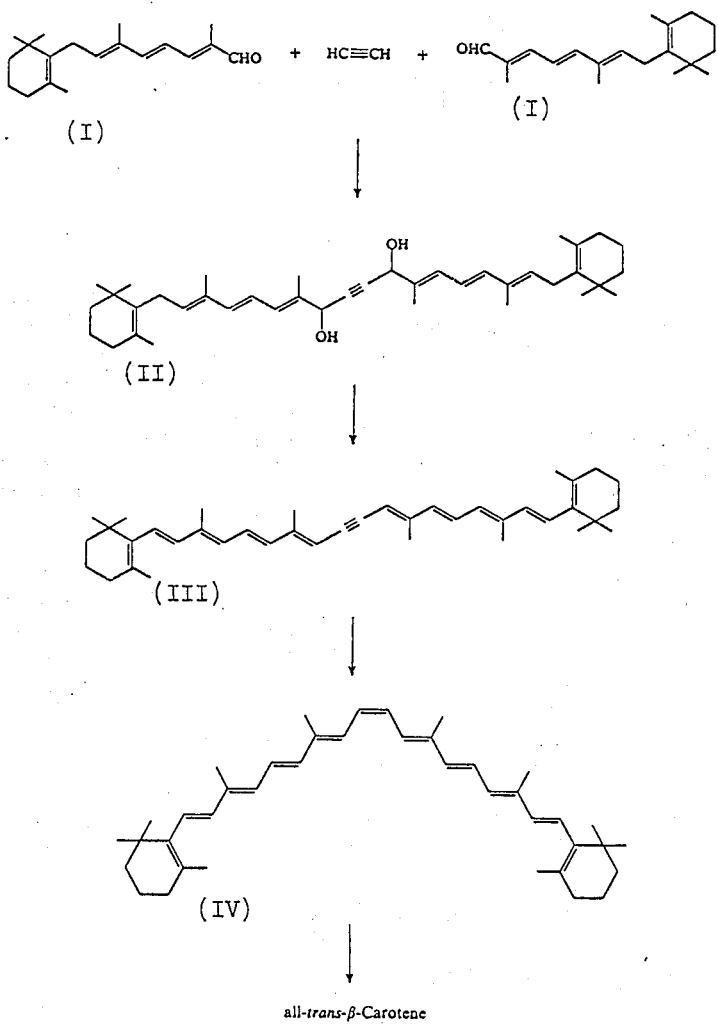

all-*trans*-β-Carotene

Two moles of β-$C_{19}$-aldehyde (I) are condensed with acetylenedimagnesium bromide to give the $C_{40}$-diol (II). The $C_{40}$-diol is converted into 15,15′ didehydro-β-carotene (III) by allylic rearrangement with simultaneous dehydration. The product is partially hydrogenated over Lindlar catalyst to give mainly 15-cis-β-carotene (IV) which is isomerized to all-trans-β-carotene by treatment in high boiling petroleum ether. While several methods of obtaining β-carotene from vitamin A have been proposed, the conditions required in these methods are extreme, the reagents are expensive, and, worst of all, the yields are low.

It is therefore an object of the present invention to provide a simple and easy method for preparing polyenes.

It is a further object of this invention to provide a method by which polyenes, and especially carotenoids, can be prepared from starting materials which are relatively cheap and readily available.

It is another object of the present invention to provide a method for producing polyenes, especially carotenoids, which require only a small number of relatively simple steps.

Other objects and advantages will be apparent to those skilled in the art from a consideration of this application, or from practicing of the invention disclosed.

Generally, the invention involves reaction of allyl alcohols with one or more disubstituted sulfides to form a sulfone, which is thereafter de-sulfonized to form the desired polyene. The reactions may be depicted as follows:

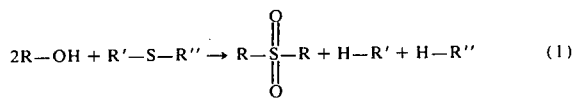

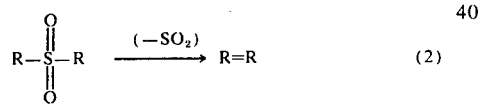

wherein R is a material having a double bond separated from the hydroxyl group by one carbon atom. R is preferably an isoprenoid containing from about 1 to 6 isoprene units, such as a terpene, sesquiterpene, or diterpene. Mixtures of different allyl alcohols may advantageously be used, depending on the product desired. R′ and R″ may be the same or different nitrogen terminated compound in which the nitrogen atom which is bound to the sulfur is also bound to a moiety which is strongly electrophilic. Preferably R and R′ are imides or imidazoles. Compounds containing suitable bound nitrogen atoms include substituted and unsubstituted pyrrole, imidazole, pyrazole, 1,2,3-triazole, 1,2,4 triazole, tetrazole, pyridine, pyridazine, pyrimidine, pyrazine, and higher nitrogen-containing heterocylcic compounds, such as carbazole; imides, such as phthalimide, succinimide and acetimide; and sulfonamides, particularly the triflamides, which are derivatives of the trifluoromethanesulfonyl group, such as N-phenyl triflamide ($C_6H_5NHSO_2$ $CF_3$). Suitable triflamides are described in Hendrickson, Tetrahedron Letters, 46: 4607 (1973) and in Hendrickson, J. Amer. Chem. Soc. 95: 3412 (1973). The sulfides of such nitrogen-containing materials can be prepared for example by reaction with sulfur chlorides in the manner described in Kalnins, Canad. J. Chem., 44: 2111 (1966) or Birkhofer, Chem. Ber., 93: 2804 (1960). They are known to react with alcohols in general, as described in Birkhofer, Chem. Ber., 99: 2070 (1966).

In preparing the present invention, the allylic alcohol (R-OH) and the disubstituted sulfide are mixed in a suitable solvent under an inert atmosphere, e.g. argon, nitrogen, etc.. The reaction proceeds at a wide range of temperatures, e.g., −50° to 50°C, preferably 0° - 40°C. It is most preferred to conduct the reaction at about room temperature, e.g. from about 15° to 35°C. Suitable solvents include lower aliphatic and cyclic ethers, such as methyl, ethyl, n- or isopropyl or the various butyl ethers, tetrahydrofuran, 1,4 dioxane, etc., halocarbons such as methylene chloride, chloroform, carbon tetrachloride, etc., and lower aromatic solvents such as benzene, toluene, ethylbenzene, etc.. Where R′ or R″ in equation 1 are imides, such as phthalimide, the ethereal solvents give relatively poor results. Those skilled in the art will know which solvents are most advantageous for particular reagents.

When the allylic alcohol is reacted with the N—S—N compounds described above, the product formed is a mixture of the sulfone

and the sulfinate ester

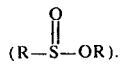

The sulfinate estere are readily converted into sulfone, e.g. by ageing with silica gel at about room temperature, to give an all-sulfone product. Other methods of making the conversion have been reported. See Braverman, Int. J. Sulfur Chem., 6: 149 (1971).

In some cases the reactivity of the nitrogen-containing groups in the sulfide is not sufficient to remove the proton from the allyl alcohol in order to obtain a satisfactory rate of production of the sulfone. Such is the case, for example, when the nitrogen-containing group is phthalimide or succinimide. This difficulty can be easily remedied by addition of a basic compound to the mixture. Suitable bases include inorganic bases, such as alkaline metal carbonates or bicarbonates, or organic bases, such as the tertiary amines or alkyllithiums.

The sulfone obtained from the first reaction is then mixed with a reactive organometallic compound of an alkali metal in a suitable solvent. The organometallic compound may be, e.g. alkyllithium or alkali amides, such as sodium, lithium, or potassium amides with alkyllithium being preferred. The alkyllithium is preferably a lower alkyl lithium, such as methyl, ethyl, propyl, or butyl lithium, n-butyl lithium being most preferred. The suitable solvents are generally the aliphatic or cyclic ethers, the lower aromatics and the lower alkanes. The halogenated hydrocarbons should not be used, as they would react with the organometallic compound. The addition of a solution of iodine or other source of positive halogen results in the splitting off of the SO₂ group, with a double bond being left in its place. The preferred agent for this purpose is iodine, but other sources of positive halogens such as bromine or chlorine can be used. Wide ranges of reaction temperatures may be employed e.g. −50° to 50°C, with peak yields being obtained at around room temperature, e.g. 15° − 35°C.

Without wishing to be bound by theory, it is believed that the alkyllithium removes a proton from the carbon atoms on either side of the sulfone group, and that the iodine or other positive or nascent halogen causes these two carbons to form a three membered ring with the sulfur, with the sulfur dioxide thereafter being split off, with formation of the double bond between these carbons. This reaction itself has been previously reported. See L. A. Paquette, Acc. Chem. Res, 1: 209 (1968) L. A. Paquette in Thyagarajan, Mechanisms of Molecular Migrations, p. 121 (1968).

The present method is particularly advantageous as compared to the prior methods of synthesizing carotenoids. Not only is it simpler and easier to run than known methods, it also gives yields of carotenoids which are above those of prior methods.

Suitable starting materials for the various carotenoids will be readily apparent to those skilled in the art. In making β-carotene, for example, R—OH in Equation 1 above will comprise vitamin A. For lycopene, R—OH would comprise:

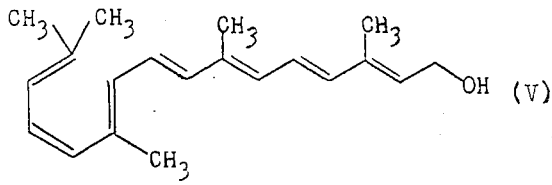

(V)

For zeaxanthin (dihydroxy -β-carotene), R—OH would comprise 3-hydroxylated vitamin A:

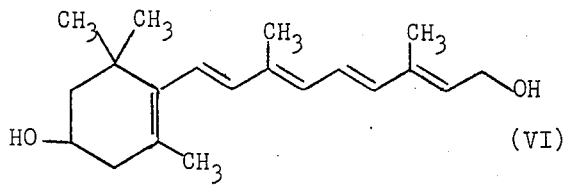

(VI)

Where there are more than one hydroxyl group in the compound, minor amounts of the non-allyl hydroxyl will also react with the —N—S—N— compound.

For non-symmetrical carotenoids, e.g. α-carotene, lutein and cryptoxanthin, mixtures of the hydroxyl terminated polyisoprene starting materials will be required, and mixtures of carotenoids will be produced. Thus for production of cryptoxanthin (monohydroxy -β-carotene), equimolar amounts of vitamin A and 3-hydroxyl substituted vitamin A (compound VI) will be required. The end product will be predominantly cryptoxanthin, and will contain minor amounts of β-carotene and zeaxanthin, which can be separated by known methods, such as chromatographic techniques or partition between solvents. Production of α-carotene would require a mixture of vitamin A and a compound of the formula:

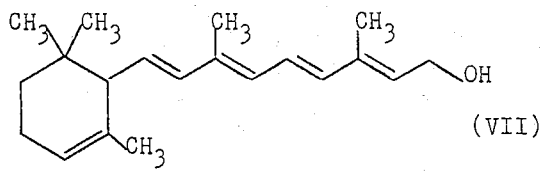

(VII)

Production of lutein (dihydroxy -α-carotene) will require a mixture of 3-hydroxyl substituted vitamin A (compound VI) and a compound corresponding to formula VII with an OH at the 3-carbon.

Normally the product of the second reaction will be a mixture of the isomers of the carotenoids. The mixture can be converted to all trans compound by heating at from about 70° − 90°C. preferably 80° − 85°C., for from a few hours to about one day. As is known in the art, this conversion into all trans can be made more rapidly by addition of a small amount of iodine or other source of positive halogen, especially with exposure to light, or by addition of a small amount of acid.

Thus the invention provides a simplified method of synthesizing compounds from materials which contain allylic hydroxyl groups. The reactions involved readily take place at room temperature, and give relatively high yields, with little or no by-product formation.

The invention will be further clarified by a consideration of the following illustrative embodiments, which are intended to be purely exemplary of the use of the invention.

EXAMPLE 1

A solution of 2.51 g of vitamin A (8.72 mmol) in 5 ml of anhydrous ether is added rapidly with stirring to a suspension of 659 mg. of 1,1′-thiodiimidazole (3.96 mmol.) in 2 ml of anhydrous ether, under an argon atmosphere. The resultant orange solution is stirred at room temperature for about 90 minutes. Ten milliliters of additional ether is added, and the solution is washed successively with 15 ml of 10% hydrochloric acid, 10 ml of 5% weight aqueous sodium carbonate, and 5 ml of saturated aqueous sodium chloride, and dried over anhydrous sodium sulfate. Removal of solvent in vacuo gives 2.59 g of an orange amorphous solid. The solid is dissolved in 120 ml of methylene chloride and stirred with 2.4 grams of Silica Gel G, made by Merck & Co. at room temperature, under argon atmosphere, for 1 hour. Filtration of the silica gel and solvent removal in vacuo gives 2.5 g of orange amorphous solid. Chromatography on 150 g of aluminum oxide with 155 ml of benzene, 155 ml of a 50/50 mixture of benzene and methylene chloride, and 30 ml of methylene chloride, elutes 475 mg of colored byproducts. Additional methylene chloride elutes 1.16 g (46% yield) of a light yellow amorphous solid identified as β-retinyl sulfone. The compound exhibits the following spectral properties: an infra red scan of the compound in carbon tetrachloride gives peaks at 2945, 1325, 1120, and 965 cm$^{-1}$. Nuclear magnetic resonance analysis in deuterated chloroform gives the following results: δ 1.05 (s, 12), [1.72 (s), 1.88 (s), 1.97 (s), 1.4 – 2.1 (m), total-30], 3.87 (d, 4, J = 8Hz), 5.53 (τ, 2, J = 8Hz), 5.9 – 7.0 (m, 10). The ultra violet spectrum in 95% ethanol shows a peak at 332 nm. The reaction is depicted thus:

to 117 mg are eluted with 315 ml of the above hexane/ether mixture. Further elution with 60 ml of the hexane/ether mixture and 225 ml of pure ether give 703 mg of a light yellow amorphous solid identified as β-retinyl sulfone, having the same spectral properties given in Example 1. This amounts to about a 74% yield.

EXAMPLE 3

Same as Example 2 except that 319 mg (3.15 mmol) of triethylamine are substituted as a base for the anhydrous potassium carbonate, and 5 ml of benzene was substituted as the solvent for the methylene chloride. The yield of β-retinyl sulfone is about 57%.

Attempts made to make β-retinyl sulfone using N,N'-thiodiphthalimide in ethyl ether and in dimethylformamide were unsuccessful. The production of β-carotene from the β-retinyl sulfone obtained in the preceding examples is illustrated in Example 4.

EXAMPLE 4

To a stirred solution of 131 mg of β-retinyl sulfone (0.218 mmol) in 6 ml of anhydrous, degassed tetrahydrofuran, at room temperature, under argon atmosphere, is added 0.21 ml of 2.1 M n-butyllithium (0.44 mmol) in hexane. The resultant very dark purple solution is stirred for 10 minutes, followed by dropwise addition of 58 mg of iodine (0.23 mmol) in 6 ml of

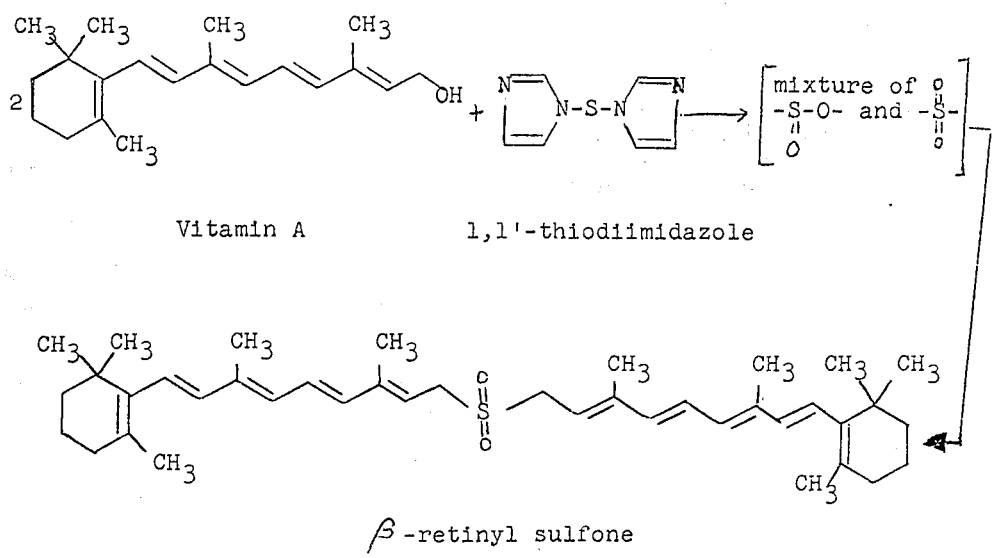

EXAMPLE 2

A mixture of 903 mg of vitamin A (3.15 mmol), 435 mg of anhydrous potassium carbonate (3.15 mmol), and 566 mg of N,N'-thiodiphthalimide (1.75 mmol) in 5 ml of methylene chloride is stirred for 5 hours at room temperature under argon atmosphere. The reaction mixture is filtered and the volume of the filtrate increased to 50 ml with methylene chloride. One gram of Silica Gel G (Merck & Co.) is added, and the mixture is stirred for 1 hour at room temperature, still under argon atmosphere. The silica gel is filtered, and the filtrate concentrated in vacuo gives 1.15 g of a yellow amorphous solid. Trituration with a mixture of 3 parts hexane to 2 parts ether by volume precipitated 139 mg of a white solid. On being chromatographed on 60 g of aluminum oxide, two yellow bands amounting tetrahydrofuran, over a period of about 13 minutes. Ethyl ether (15 ml) is added to the reaction mixture, and the resultant solution is washed with 10 ml of water and 10 ml of saturated aqueous sodium chloride, and dried over anhydrous sodium sulfate. Removal of the solvent in vacuo gives 131 mg of a dark red semisolid. Elution with 35 ml of benzene on a 16cm × 1.3cm chromatography column of aluminum oxide gives 33 mg of β-carotene (28% yield) as a mixture of stereo isomers. A suspension of this material in heptane under argon atmosphere is heated at 80° – 85°C overnight. Recrystallization of the product from benzene - methanol (about 1:3 by volume) gives dark red crystals, mp 179° – 80°C (evacuated capillary). Compared with a sample of natural all-trans β-carotene and a mixture of the natural and the above-produced synthetic all-trans β-carotene, all have the same melting point. In addition, the natural and synthetic sample have identical infra-red, nuclear magnetic resonance, ultra violet, visible and mass spectra, and were identical on three separated thin layer chromotography systems: on alumina, eluted with benzene; on silica gel, eluted with a 9 to 1 mixture of hexane/methylene chloride; and on silica gel eluted with benzene.

EXAMPLE 5

In this example n-butyl lithium is used as a base in place of the triethylamine of Example 3 or the anhydrous potassium carbonate of Example 2. To a solution of 1723 mg (20 mmol) of 1,1-dimethyl allyl alcohol in 40 ml of methylene chloride at 0°C, is added 9.8 ml of a 2.1 M solution of n-butyllithium (20.6 mmol) in hexane. The mixture is warmed to room temperature, and 3.39 g (10.5 mmol) of N,N'-thiodiphthalimide is added slowly. The resultant mixture is stirred at room temperature 11 hours, filtered, and the filtrate is concentrated in vacuo. It is washed twice with 50 ml portions of pentane, and again concentrated in vacuo. A brown oil (1.4 g) is obtained, which is dissolved in 80 ml of methylene chloride and stirred with 0.5 g of silica gel for 19 hours at room temperature. Filtration and concentration give 1.32 g of a brown oil. This oil is filtered over alumina and crystallized from pentane to give 834 mg (41.5% yield) of white needles of dimethyl allyl sulfone having the following formula:

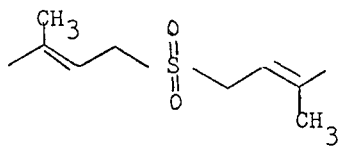

In this case there was a rearrangement of the double bond. The above sulfone can then be reacted with 8.26 mmol of n-butyllithium and 4.13 mmol of iodine in the manner of Example 4 to give a compound of the structure:

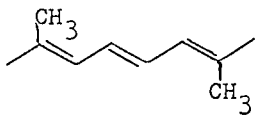

EXAMPLE 6

To 3.08 g of the terpene linalool (20 mmol) in 40 ml of methylene chloride, is added 9.8 ml (20.6 mmol) of a 2.1 M solution of n-butyllithium in hexane. Addition of 3.56 g (11 mmol) of N,N'-thiodiphthalimide followed by stirring at room temperature for 11 hours and concentration in vacuo gives 2.99 g of a brown oil. A 2.04 g sample of that oil is dissolved in 100 ml methylene chloride, mixed with 2 g silica gel and stirred for 22 hours, and concentrated in vacuo to yield 1.90 g of a brown oil. The residual linalool is distilled off to give 1.25 g of disubstituted sulfone, which comprises a mixture of stereo isomers. Reaction with n-butyl lithium and iodine in the manner of Example 4 will yield a diterpene.

While a number of particular embodiments of the present invention have been described herein, they are intended to merely be exemplary, and the true scope and spirit of the invention is indicated by the following claims.

We claim:
1. A method of preparing polyenic organic compounds, comprising reacting an allyl alcohol with a sulfide of the following formula
R' — S — R"
in which R' and R" are the same or different nitrogen-containing substituents, bound to sulfur through a nitrogen atom, the remainder of R' and R" being electrophilic, to produce an allylic sulfone, reacting said sulfone with an organometallic compound selected from the group of alkyllithiums and alkali metal amides and a halogen selected from the group of bromine, chlorine and iodine.

2. The method of claim 1 in which the allyl alcohol is a compound of the following structure:

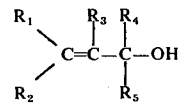

in which $R_1$–$R_5$ are alkyl, alkenyl or hydrogen.

3. The method of claim 2, in which $R_1$ represents from about 1 to 6 isoprene units, $R_2$ represents methyl, and $R_3$–$R_5$ represent hydrogen.

4. The method of claim 2, in which R' and R" are selected from the group of pyrrole, imidazole, pyrazole, 1,2,3-triazole, 1,2,4-triazole, tetrazole, carbazole, phthalimide, succinimide, succinimide, acetimide, trifluoromethylsulfonamides.

5. The method of claim 2, in which R' and R" are selected from the group of imidazole, phthalimide and succinimide.

6. The method of claim 2, in which the allyl alcohol is reacted with the sulfide in the presence of a base.

7. The method of claim 2, in which the reaction product of the allyl alcohol and the sulfide comprises a mixture of allyl sulfone and allyl sulfinate ester, said sulfinate ester being converted to allyl sulfone prior to reaction with the organometallic compound.

8. The method of claim 2 in which the organometallic material is a lower alkyllithium.

9. A method of preparing carotenoids, comprising reacting an allyl alcohol having the following formula:

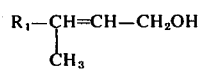

wherein $R_1$ represents from about 1 to 6 isoprene units, with a sulfide having the following formula:
$R_2$ — S — $R_3$
in which $R_2$ and $R_3$ are the same or different nitrogen-containing substituents, bound to sulfur through a nitrogen atom, the remainder of R' and R", being electrophilic, to produce a mixture comprising an allyl sulfone and sulfinate ester, converting said sulfinate ester to an allyl sulfone, reacting said sulfone with an organometallic compound selected from the group of alkyllithiums and alkali metal amides and a halogen selected from the group of bromine, chlorine and iodine.

10. The method of claim 9, in which $R_2$ and $R_3$ are selected from the group of pyrrole, imidazole, pyrazole, oxazole, 1,2,3-triazole, 1,2,4-triazole, tetrazole, carbazole, phthalimide, succinimide, acetimide, and trifluoromethylsulfonamides.

11. The method of claim 9, in which $R_2$ and $R_3$ are selected from the group of imidazole, phthalimide, and succinimide.

12. The method of claim 9, in which the allyl alcohol is reacted with the sulfide in the presence of a base.

13. The method of claim 9, in which the allyl alcohol is vitamin A and the carotenoid produced is β-carotene.

14. The method of claim 13, in which the organometallic compound is a lower alkyllithium.

15. The method of claim 14, in which the organometallic compound is n-butyllithium.

16. The method of claim 7, in which said sulfinate ester is converted to an allyl sulfone by contacting said sulfinate ester with silica gel.

17. The method of claim 9, in which said sulfinate ester is converted to an allyl sulfone by contacting said sulfinate ester with silica gel.

* * * * *